(12) United States Patent
Berry

(10) Patent No.: US 7,608,078 B2
(45) Date of Patent: Oct. 27, 2009

(54) EXPANSION APPARATUS FOR ADJUSTABLE SPINAL IMPLANT

(75) Inventor: Bret M. Berry, Jacksonville, FL (US)

(73) Assignee: Warsaw Orthopedic, Inc.

( * ) Notice: Subject to any disclaimer, the term of this patent is extended or adjusted under 35 U.S.C. 154(b) by 391 days.

(21) Appl. No.: 11/286,887

(22) Filed: Nov. 23, 2005

(65) Prior Publication Data

US 2006/0084975 A1    Apr. 20, 2006

Related U.S. Application Data

(63) Continuation of application No. 10/663,554, filed on Sep. 16, 2003.

(60) Provisional application No. 60/412,730, filed on Sep. 23, 2002.

(51) Int. Cl.
*A61B 17/56* (2006.01)

(52) U.S. Cl. .................. 606/86 A; 606/99; 606/53; 81/57.59

(58) Field of Classification Search .................. 606/53, 606/99, 104, 88, 206, 86 A, 246; 623/17.15–17.16; 269/61, 242, 6, 134, 135, 136; 81/352, 387, 81/389, 57.29, 176.1; 294/119.1, 16; 74/817, 74/73, 842

See application file for complete search history.

(56) References Cited

U.S. PATENT DOCUMENTS

| 273,340 | A | 3/1883 | Bishoprick |
|---|---|---|---|
| 359,378 | A | 3/1887 | Ballou |
| 608,220 | A | 8/1898 | Plagman |
| 664,911 | A | 1/1901 | Voss |
| 740,868 | A | 10/1903 | Johnson |
| 751,606 | A | 2/1904 | Brammer |
| 858,292 | A | 6/1907 | Jackson |
| 858,894 | A | 7/1907 | Moss |
| 1,117,167 | A | 11/1914 | Corell |
| 1,362,550 | A | 12/1920 | Walter |
| 1,415,731 | A | 5/1922 | Terry |
| 2,109,696 | A | 3/1938 | Hackethal |
| 2,400,712 | A | 5/1946 | Prather et al. |
| 3,176,908 | A | 4/1965 | Bowdish |
| 4,762,031 | A | 8/1988 | Bradley |
| 5,571,192 | A | 11/1996 | Schonhoffer |
| 5,702,453 | A | 12/1997 | Rabbe et al. |

(Continued)

FOREIGN PATENT DOCUMENTS

DE           3023942 A1       1/1982

*Primary Examiner*—Thomas C Barrett
*Assistant Examiner*—James L Swiger

(57) ABSTRACT

An expansion assembly expands a vertebral implant. The vertebral implant has an inner cylindrical assembly adapted for insertion into an outer cylindrical assembly having an outer wall. The vertebral implant is expandable along an implant axis defined by the outer and inner cylindrical assemblies. The expansion assembly comprises an axle having proximal and distal end portions and an axle axis defined between the proximal and distal end portions. The expansion assembly further comprises a gear arranged about the axle axis at the proximal end portion of the axle and adapted to rotate about the axle axis to cause the inner cylindrical assembly to expand the vertebral implant. The engagement assembly also comprising a first engaging portion adapted to engage the inner cylindrical assembly and a second engaging portion adapted to engage the gear externally of the outer wall of the outer cylindrical assembly.

20 Claims, 4 Drawing Sheets

U.S. PATENT DOCUMENTS

| | | | |
|---|---|---|---|
| 5,702,455 A * | 12/1997 | Saggar | 623/17.15 |
| 5,732,992 A | 3/1998 | Mauldin | |
| 5,776,197 A | 7/1998 | Rabbe et al. | |
| 5,776,198 A | 7/1998 | Rabbe et al. | |
| 5,989,259 A | 11/1999 | Penenberg et al. | |
| 5,989,290 A | 11/1999 | Biedermann et al. | |
| 6,190,413 B1 | 2/2001 | Sutcliffe | |
| 6,190,414 B1 * | 2/2001 | Young et al. | 623/17.15 |
| 6,277,123 B1 | 8/2001 | Maroney et al. | |
| 6,344,057 B1 | 2/2002 | Rabbe et al. | |
| 6,478,800 B1 | 11/2002 | Fraser et al. | |
| 6,692,495 B1 * | 2/2004 | Zacouto | 606/247 |
| 6,716,218 B2 | 4/2004 | Holmes et al. | |
| 6,752,832 B2 * | 6/2004 | Neumann | 623/17.15 |
| 6,902,579 B2 | 6/2005 | Harms et al. | |
| 7,169,153 B2 | 1/2007 | Keller | |
| 2002/0058944 A1 | 5/2002 | Michelson | |
| 2002/0082695 A1 | 6/2002 | Neumann | |
| 2003/0225416 A1 | 12/2003 | Bonvallet et al. | |
| 2003/0229355 A1 | 12/2003 | Keller | |

\* cited by examiner

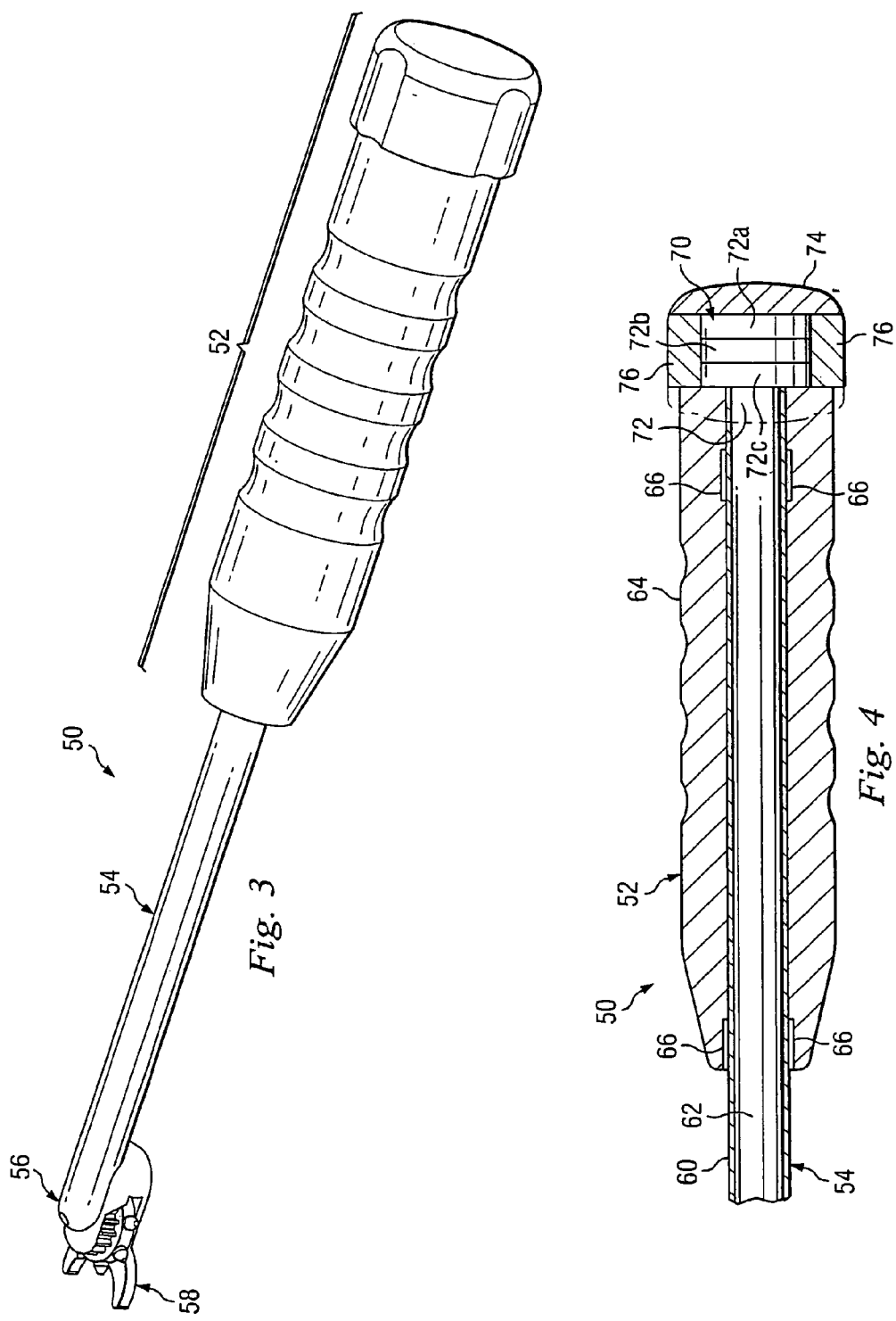

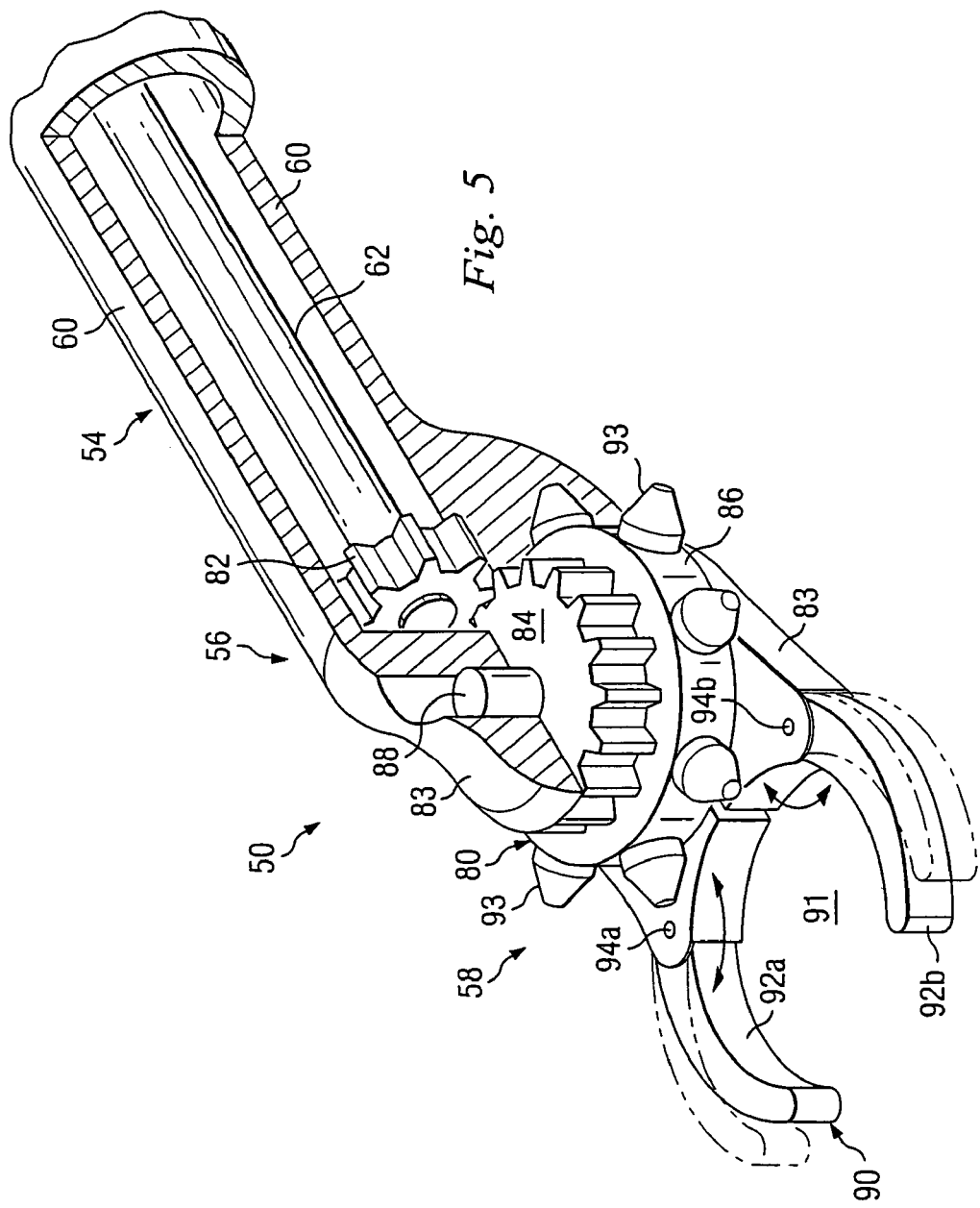

EXPANSION APPARATUS FOR ADJUSTABLE SPINAL IMPLANT

CROSS REFERENCE

This application is a Continuation of U.S. Ser. No. 10/663,554, filed on Sep. 16, 2003 and incorporated by reference herein, which claims the benefit of U.S. Provisional Application No. 60/412,730 filed on Sep. 23, 2002 and incorporated by reference herein.

FIELD OF THE INVENTION

The present invention concerns medical procedures and instruments used during surgery. More particularly, a novel apparatus and method is provided for adjusting an adjustable vertebral implant.

BACKGROUND

A variety of spinal injuries and deformities can occur due to trauma, disease or congenital effects. For example, one type of spinal deformity, a kyphosis, involves a prolapse of the vertebral column towards the front of the body, often caused by the destruction of the vertebral body itself. This destruction can be in the form of a trauma type injury, such as a fracture or burst injury to the vertebral body, or a non-traumatic deformity caused by a tumor or a degeneration of the bone in the vertebral body.

Treatment of a kyphosis in the thoracic or lumbar spine appears now to be best achieved through an anterior approach, particularly in order to avoid some of the more severe complications associated with support or replacement of a damaged vertebral body. In most treatments of a kyphosis, a high degree of anterior reconstruction of the spine is required, most frequently involving total removal of the damaged vertebral body. In a typical anterior approach, partial or total ablation of the vertebral body and the two adjacent vertebral discs is carried out. Following this vertebrectomy, a vertebral implant assembly may be used to restore the vertebral column to the correct orientation.

One implant that may be used is disclosed in U.S. Pat. No. 6,344,057 to Rabbe et al. ("Rabbe patent"), which is hereby incorporated by reference. The implant disclosed in the Rabbe patent is an adjustable vertebral implant assembly configured to span the void created by the removed vertebral body and discs. The assembly includes a thin-walled tubular body which defines a hollow interior and further includes endplates with end surfaces configured to engage the tubular body between the adjacent vertebrae. In some embodiments, the end surfaces defines a bore through the endplate.

Current surgical spinal reconstruction techniques can use a plurality of wrenches to expand or otherwise manipulate rotationally adjustable implants, such as the assembly disclosed in the Rabbe patent. However, a wrench requires lateral translation which, in the confined area of the wound, can require an enlarged wound and increased labor and time. It must also relocate and reattach to the implant after each turn, which is both difficult and time consuming.

SUMMARY

In one embodiment of the present disclosure, an expansion assembly expands a vertebral implant. The vertebral implant has an inner cylindrical assembly adapted for insertion into an outer cylindrical assembly having an outer wall. The vertebral implant is expandable along an implant axis defined by the outer and inner cylindrical assemblies. The expansion assembly comprises an axle having proximal and distal end portions and an axle axis defined between the proximal and distal end portions. The expansion assembly further comprises a gear arranged about the axle axis at the proximal end portion of the axle and adapted to rotate about the axle axis to cause the inner cylindrical assembly to expand the vertebral implant. The engagement assembly also comprising a first engaging portion adapted to engage the inner cylindrical assembly and a second engaging portion adapted to engage the gear externally of the outer wall of the outer cylindrical assembly.

In another embodiment, a method for installing a vertebral implant between adjacent vertebrae comprises providing a vertebral implant having an inner cylindrical body extending into an outer cylindrical body. The outer cylindrical body has an outer wall and the bodies defining an implant axis. The method further includes providing an expansion assembly. The expansion assembly comprises an axle having proximal and distal end portions and an axle axis defined between the proximal and distal end portions. The expansion assembly also includes a secondary gear assembly attached to the proximal end portion and a main gear assembly engaged with the secondary gear assembly externally of the outer wall. The method further includes engaging the main gear assembly with the inner cylindrical body and rotating the axle about the axle axis to cause the inner cylindrical body to move relative to the outer cylindrical body along the implant axis.

In still another embodiment, an instrument is adapted for installing a vertebral implant. The implant has at least one outer tubular assembly threadedly engaged with an inner tubular assembly. The instrument comprises an axle having proximal and distal ends and an axle axis defined between the proximal and distal ends. The instrument also comprises a gear assembly connected to the proximal end of the axle and adapted to rotate the inner tubular assembly to expand the vertebral implant. The inner tubular assembly is rotated without extending the gear assembly into the at least one outer tubular assembly.

BRIEF DESCRIPTION OF THE DRAWINGS

FIG. 3 is a perspective view of an expansion apparatus according to an embodiment of the present invention.

FIG. 4 is a cross-sectional view of a portion of the expansion apparatus of FIG. 3.

FIG. 5 is a partial cross-section of a portion of the expansion apparatus of FIG. 3.

DETAILED DESCRIPTION

Figure 1:
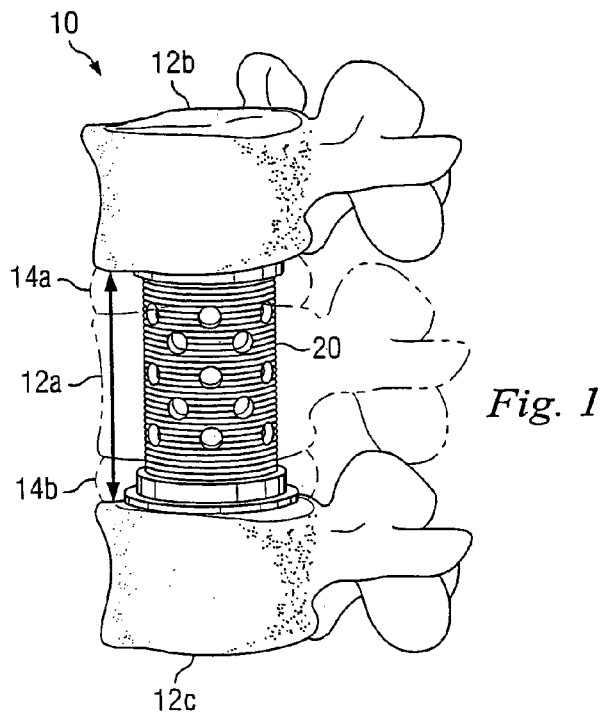
FIG. 1 is an perspective view of a destroyed vertebral body within a vertebral column (in shadow) and a vertebral implant assembly according to one embodiment of the present invention positioned within the vertebral column.

Referring to FIG. 1, a vertebral column 10 includes a damaged vertebra 12a (shown in phantom) extending between a vertebra 12b and a vertebra 12c. An intervertebral disc 14a (shown in phantom) extends between vertebrae 12a and 12b, and an intervertebral disc 14b (shown in phantom) extends between vertebrae 12a and 12c. In a surgical excision, the vertebra 12a can be removed together with discs 14a and 14b creating a void between the two intact vertebra 12b and 12c. This procedure may be performed using an anterior, anterolateral, or other approach known to one skilled in the art. A vertebral implant assembly 20 as described in the Rabbe patent can then be provided to fill the void between the two intact vertebrae 12b and 12c.

Figure 2:
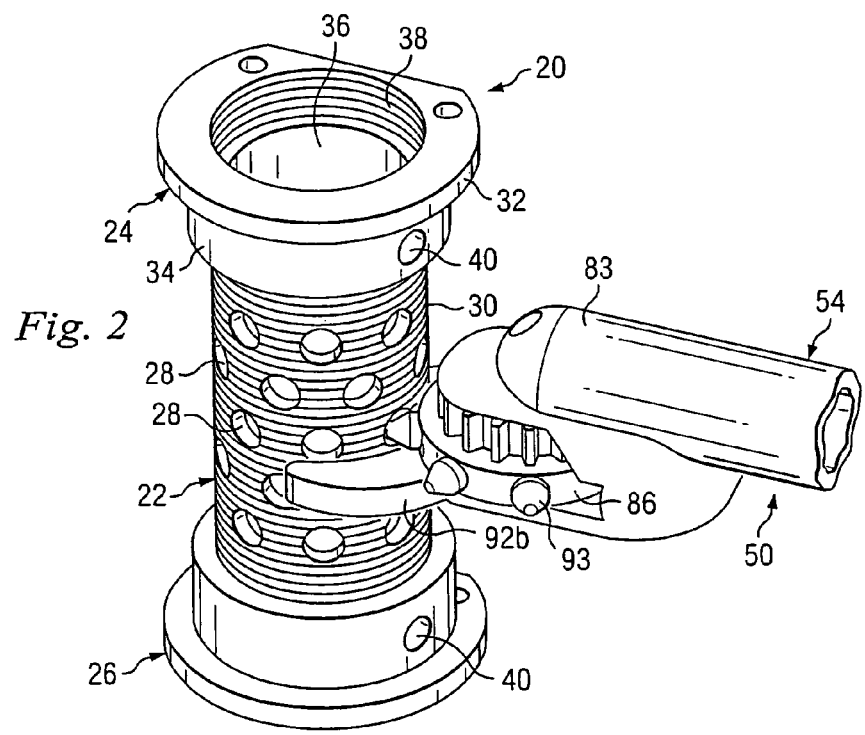
FIG. 2 a perspective view of a vertebral implant assembly coupled with a portion of an expansion apparatus according to one embodiment of the present invention.

Referring now to FIG. 2, the vertebral implant assembly 20 is shown as a turnbuckle in accordance with one embodiment of the present invention. The implant assembly 20 generally includes a threaded tubular body 22 extending between threaded endplate assemblies 24 and 26. The threaded tubular body 22 is provided with a plurality of apertures 28 that may be used for installation of the assembly 20 and that may also provide an avenue for bone or tissue ingrowth to further enhance the stability of the replacement assembly after implantation. In the present embodiment, the opposite ends of the tubular body 22 are formed into external threads 30. The threads 30 may extend from each opposite end over most or all of the length of the tubular body 22 and may be configured to threadedly engage endplate assemblies 24 and 26.

The endplate assembly 24 may include a flange 32, which may cover a substantial load-bearing area of the endplates of the adjacent intact vertebral bodies. A cylinder 34 may be integrally formed with flange 32 to extend toward the threaded tubular body 22 when the endplate assembly 24 is placed within the excised vertebral space. The cylinder 34 and flange 32 define a bore 36 there through. The inside surface of the bore 36 is provided with internal threads 38 which are configured to mate with the external threads 30 of the tubular body 22. In one embodiment, the threads 38 extend along the entire length of the cylinder 34 and into the flange 32. Endplate assembly 26 may be configured similar or identical to endplate assembly 24 and therefore will not be described in detail. The endplate assemblies 24 and 26 may further include one or more apertures 40 configured to engage a holding instrument (as described below for FIGS. 6a and 6b).

In one specific embodiment, the external threads 30 on the threaded tubular body 22 may be cut in opposite directions (e.g., right handed and left handed) so that the endplates can be drawn together or apart by rotating only the body. Thus, as the body is rotated in one direction, the threads 30 at each of the ends engage the internal threads 38 of each of the end caps 24 and 26 in the proper direction to draw the end caps together. Alternatively, the handedness of the threads 30 can be the same at each end so that it is necessary to individually thread each end cap in opposite directions onto the tubular body 22. The disadvantage of this arrangement is that it is more difficult to adjust the height of the total assembly 20 while maintaining the proper orientation of each of the endplate assemblies 24 and 26. An advantage is that in situ the assembly is unable to unthread itself. Further details of the assembly 20 and its operation are described in the embodiments shown in the Rabbe patent.

The assembly 20 may be inserted into the vertebral column (as shown in FIG. 1) and then expanded to achieve the desired fit and alignment between the adjacent intact vertebrae. In one embodiment, expansion of the assembly can be achieved by rotating the tubular body 22 using an expander apparatus 50 as shown in FIG. 3.

Referring now to FIG. 3, in accordance with one embodiment of the present invention, the expander apparatus 50 includes a handle section 52, an extension section 54, a main gear box 56 and an engager 58. The expander apparatus 50 may allow the assembly 20 to be adjusted without the use of lateral movement, thereby reducing the size of a patient's wound and decreasing the time and labor involved to complete the procedure.

Referring to both FIG. 3 and FIG. 4, the handle section 52 can receive and enclose a portion of the extension section 54. In the present embodiment, the extension section 54 may comprise an outer casing 60 through which an interior axle 62 may extend. The handle section 52 may include a handle 64 that receives, surrounds and rotationally engages the outer casing 60 of the extension section 54 through one or more bushings 66. It is understood that in other embodiments, the rotational engagement of the outer casing 60 may be accomplished using ball bearing assemblies and/or the material comprising the handle 64. Although not shown, in some embodiments, the handle 64 may be separated into two independent portions, with one portion being fixed to the outer casing 60 to secure and position the expander apparatus 50 during use, and the other portion being free to rotate for providing the rotational force discussed below.

In the present embodiment, the handle section 52 may further include a distally located selector gear box 70. The selector gear box 70 may include a set or plurality of gears 72a, 72b, 72c configured to selectively engage with the distal end of the interior axle 62 of the extension section 54. Each of the gears 72a, 72b, and 72c may be of a different size so that a user of the expander apparatus 50 may choose from a range of selectable gear ratios, enabling the user to achieve a desired speed or torque for adjusting the vertebral implant assembly 20. The selector gear box 70 may be configured to engage with a cap member 74. The cap member 74 can be both axially and rotationally movable about the handle 64 and can further include a gear selection member 76 which, as the cap member 74 is moved, can engage any of the different gears 72a, 72b, or 72c to create the desired gear ratio.

Although the present embodiment depicts three gears, it is understood that in other embodiments a fewer or a greater number of gears may be used. Further, any of a variety of gear train systems may be employed incorporating a variety of gear components such as a planetary gear systems, a layshaft, a clutch, a worm gear system, a bevel gear system, a rack and pinion system, or other gear based systems. In the present embodiment, the cap member 74 rotates or translates about the handle 64 to select a particular gear, but other gear selection mechanisms can also be used. In some embodiments, the selector gear box may not be located in the handle section 52, but rather, may be included in the extension section 54 or elsewhere in the expander tool 50.

Although not shown, in another embodiment, the selector gear box 70 may be omitted and the distal end of the axle 62 may be fixedly engaged with the gear selection cap 74 and/or a rotating portion of the handle section 52. In this embodiment, the rotation of the axle 62 may be directly driven by rotation of the gear selection cap 74. In still another embodiment, the axle 62 may be driven by a motor coupled to the axle 62 or to the selector gear box 70.

Referring now to FIG. 5, while one end of the extension section 54 engages with the handle section 52, the opposite end may engage with the main gear box 56. The main gear box 56 may include a main gear/tooth assembly 80 and a secondary gear assembly 82. The main gear/tooth assembly 80 can be partially enclosed and secured within a casing 83, and can include a gear section 84 coaxially attached to a toothed section 86. The casing 83 may include a pin 88 about which the main gear/tooth assembly 80 can rotate. In the present embodiment, the rotational axis of the pin 88 and the gear section 84 may be aligned perpendicular to the rotational axis of the axle 62, although different embodiments may have different arrangements.

The secondary gear assembly 82 may be attached to the proximate end of the interior axle 62, opposite from the end engaged with the selector gear box 70, and may rotate about the axis of the axle 62. The secondary gear assembly 82 may engage with the gear section 84 of the main gear/tooth assembly 80 causing any rotational force from the axle 62 to be transferred to the main gear/tooth assembly 80.

Referring to FIGS. 2 and 5, the main gear box 56 can be further connected to the engager 58. The casing 83 of the main gear box 56 may be attached to a positioning mechanism 90, which in the embodiment of FIG. 2 is shaped like a semicircle with opposing arc portions 92a and 92b. The arc portions 92a and 92b can define a cross-section of an engagement area 91 into which the implant assembly 20 may be positioned. The positioning mechanism 90 is shaped to mate with the tubular body 22 of the implant assembly 20, allowing the tubular body 22 to rotate while assisting in maintaining the general position and proximity of the engager 58 to the tubular body 22.

As described above, the casing 83 may cover only a portion of the main gear/tooth assembly 80. The other portion, which can include the tooth section 86, may extend into the engagement area 91 of the engager 58. The tooth section 86 may include a plurality of teeth 93 that are sized, spaced, and shaped to engage the apertures 28 on the tubular body 22 when the tubular body 22 is positioned in the engagement area 91. With the endplate assemblies at least tentatively affixed to the adjacent vertebral endplates, the tubular body 22 can rotate as the tooth section 86 is rotated. Furthermore, the positioning mechanism 90 and the arrangement of the apertures 28 can minimize any translation of the tubular body 22, ensuring that the next tooth 93 easily locates and engages the next aperture 28, to thereby maintain the rotation. In the present embodiment, the teeth 93 are radially arranged on the tooth section 86 in a gear-like configuration. In other embodiments, a toothed belt or another gripping mechanism can be used to drive the rotation of the tubular body 22.

Referring more specifically to FIG. 5, in some embodiments, the positioning mechanism 90 is shaped more like a "C." In these embodiments, the positioning mechanism 90 also helps to prevent the engager 58 from accidentally disengaging from the replacement assembly 20. In one embodiment, the opposing arc portions 92a, 92b are selectively pivotable about pins 94a and 94b with friction keeping the arc portions 92a, 92b either open or closed. In the open position, the tubular body 22 can be positioned in or removed from the engagement area 91. In the closed position, the arc portions 92a and 92b aid in keeping the positioning mechanism 90 engaged to the tubular body 22 while the body rotates. It is understood, that other embodiments may use a clip, a spring, or some other means of engagement to selectively allow the positioning mechanism 90 to remain engaged.

In some embodiments, the positioning mechanism 90 may be configured to more securely maintain the desired position of implant assembly 20. For example, the positioning mechanism 90 may extend laterally along the tubular body 22 to restrain the assembly 20 from pivoting about its longitudinal axis. Another example (e.g. FIGS. 6a and 6b) may include a second positioning mechanism 90 extending from the casing 83 in which case the assembly 20 can be held in position by arc positions both above and below the tooth section 86.

Referring now to FIGS. 1-5, in operation, once the implant assembly 20 is placed in position between the endplates of the two adjacent vertebrae 12b and 12c (as shown in FIG. 1), the expander apparatus 50 may be positioned within the surgical area proximate to the implant assembly 20. It is understood, however, that in some instances the expander apparatus 50 can be used to facilitate the placement of the assembly 20 inside the vertebral column 10. The expander apparatus 50 is positioned so that the engager 58 is engaged with the tubular body 22 of the implant assembly 20. Specifically, at least one of the teeth 93 may engage one of the apertures 28. The handle 60 can extend away from the vertebral column 10, for example, in an anterior surgical approach, the handle may be positioned in the anterior area of the patient, within easy reach of the surgeon.

After the expander apparatus is in place, the surgeon can rotate or axially translate the cap member 74 to engage the appropriate gear 72a, 72b, 72c to achieve the desired gear ratio, although it is understood that in some embodiments the selector gear box 70 can be omitted. The surgeon can then turn either the handle 64 or the rotatably movable portion of the handle 64 around the axis of the interior axle 62 to expand (or contract, if necessary) the implant assembly 20. Specifically, the rotation of the handle 64 or handle portion is transferred through the gear box 70 to rotate the axle 62. The axle, in turn, rotates the secondary gear assembly 82, which rotates the gear section 84. The rotation of the gear section 84, causes the fixedly attached tooth section 86 to rotate which, in turn moves the teeth 93. With the endplate assemblies 24 and 26 held immovably in place by compression of the vertebral endplates, by structural features of the endplate assemblies 24 and 26, or by mechanical means, the movement of the teeth 93 can cause the tubular body 20 to rotate which may cause the endplate assemblies 24 and 26 to move relative to one another, thereby expanding, contracting, or otherwise adjusting the implant assembly 20.

Figure 6A:
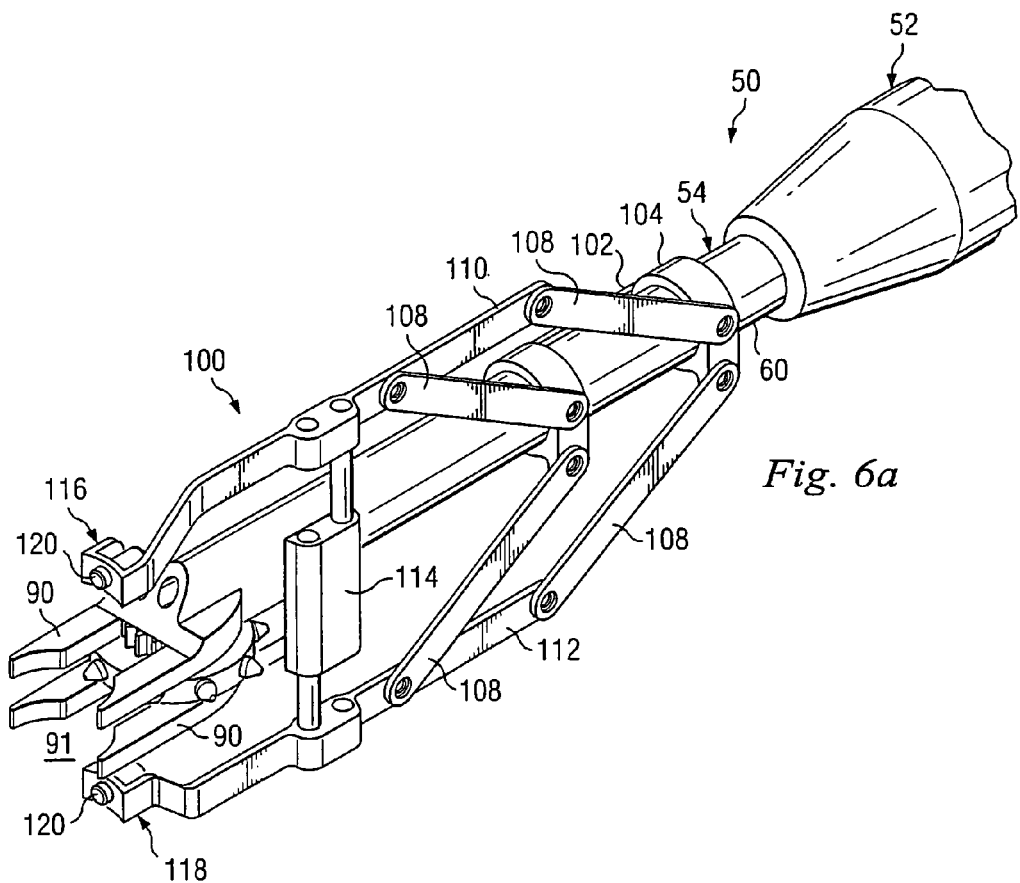
FIGS. 6a and 6b are perspective views of a holding instrument used with the expansion apparatus of FIG. 3.
Figure 6B:
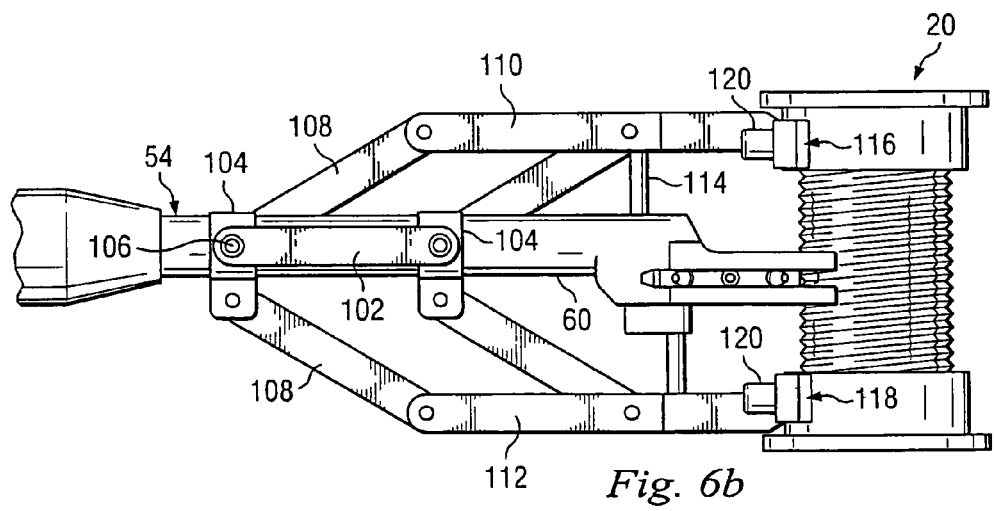

Referring now to FIGS. 6a and 6b, in this embodiment, a holding instrument 100 may be coupled to the expander apparatus 50 to hold the implant assembly 20 in position during the expansion, all the while minimizing backlash or lateral movement of the assembly 20. The holding instrument can be attached to the extension section 54 by an attachment device 102 which may include one or more rings 104 configured for fastening to the outer casing 60. The one or more rings 104 may be fixedly attached to the extension section with one or more fastening mechanisms 106 which can be, for example, screws. In one alternative embodiment, to avoid interference with the interior axle 62 running through the extension section 54, the fastening mechanisms 106 may engage a protrusion (not shown) extending from the outer casing 60.

A plurality of expansion members 108 may connect the attachment device 102 to a pair of alignment arms 110 and 112. Each expansion member 108 may be a rigid bar pivotally connected at one end to the attachment device 102 and at the opposite end to one of the alignment arms 110 or 112. In alternative embodiments, the expansion member may be a spring, an elastic member, or another mechanism capable of expanding with the alignment arms 110 and 112 as the implant 20 is expanded. An alignment member 114 may further extend between the alignment arms 110 and 112 and may be adjustable to maintain a relatively parallel alignment of the alignment arms. Each of the alignment arms 110 and 112 extend toward the engagement area 91 where the ends of each alignment arm 110 and 112 are configured with holding assemblies 116 and 118, respectively. The holding assemblies 116 and 118 may be arc-shaped to accept the assembly 20 and may further include fasteners 120 for engaging the apertures 40 on the endplate assemblies 24 and 26 to maintain the assembly 20 in a generally rigid vertical position while the assembly 20 is expanded. The fasteners may be, for example, pins, screws, or clamps. In some embodiments, the holding assemblies 116 and 118 may fasten to the endplate assemblies 24 and 26 without engaging the apertures 40.

Referring still to FIGS. 6a and 6b, in operation, once the implant assembly 20 is placed in position between the endplates of the two adjacent vertebrae 12b and 12c (as shown in FIG. 1), the expander apparatus 50 with the attached holding instrument 100 may be positioned within the surgical area proximate to the implant assembly 20. It is understood, however, that in some instances the expander apparatus 50 and holding instrument 100 can be used to facilitate the placement of the assembly 20 inside the vertebral column 10. The expander apparatus 50 is positioned so that the engager 58 is engaged with the tubular body 22 of the implant assembly 20. Specifically, at least one of the teeth 93 may engage one of the apertures 28. To further secure the implant assembly 20, the pins 120 may be engaged with the apertures 40 on the endplate assemblies 24 and 26. The handle 60 can extend away from the vertebral column 10, for example, in an anterior surgical approach, the handle may be positioned in the anterior area of the patient, within easy reach of the surgeon.

After the expander apparatus is in place, the surgeon can rotate or axially translate the cap member 74 to engage the appropriate gear 72a, 72b, 72c to achieve the desired gear ratio. It is understood that in some embodiments the selector gear box 70 can be omitted. The surgeon can then rotate either the handle 64 or the rotatably movable portion of the handle 64 along the axis of the interior axle 62 to expand (or contract, if necessary) the implant assembly 20. Specifically, the rotation of the handle 64 or handle portion is transferred through the gear box 70 to rotate the axle 62. The axle, in turn, rotates the secondary gear assembly 82, which rotates the gear section 84. The rotation of the gear section 84, causes the fixedly attached tooth section 86 to rotate which, in turn moves the teeth 93.

With the endplate assemblies 24 and 26 held immovably in place by the holding instrument 100, the movement of the teeth 93 can cause the tubular body 20 to rotate, which in turn can cause the endplate assemblies 24 and 26 to move relative to one another, thereby expanding (or contracting, if necessary) the implant assembly 20. As the implant assembly 20 expands, the expansion members 108 may pivot to allow the alignment arms 110 and 112 to move apart while remaining in relatively parallel alignment. As the alignment arms 110 and 112 move, the alignment member 114 may adjust to further preserve the parallel alignment of the alignment arms 110 and 112. After the implant assembly 20 has attained the desired height, the pins may be removed from the apertures 40, disconnecting the holding instrument 100 from the implant assembly 20.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A system comprising:
    a vertebral implant comprising:
        at least one outer tubular assembly threadedly engaged with an inner tubular assembly, each of the at least one outer tubular assembly and the inner tubular assembly including parallel bone engagement surfaces,
    an instrument comprising:
        an axle having proximal and distal ends and an axle axis defined between the proximal and distal ends;
        a gear assembly comprising a plurality of gears connected to the proximal end of the axle and engaged with the inner tubular assembly with a set of radially spaced pins, the gear assembly adapted to vertically displace the inner tubular assembly with respect to the at least one outer tubular assembly to expand the vertebral implant; and
        a fastener sized to extend into only one through aperture in an outer wall of the at least one outer tubular assembly,
    wherein the inner tubular assembly is vertically displaced without extending the gear assembly into the at least one outer tubular assembly,
    wherein the fastener prevents the at least one outer tubular assembly from rotating relative to the instrument when the gear assembly vertically displaces the inner tubular assembly with respect to the at least one outer tubular assembly to expand the vertebral implant.

2. The system of claim 1 wherein the gear assembly includes a main gear assembly for engaging the inner tubular assembly and a secondary gear assembly connected to the proximal end of the axle.

3. The system of claim 2 wherein the main gear assembly includes teeth adapted to engage the secondary gear assembly.

4. The system of claim 3 wherein the secondary gear assembly is adapted to rotate about the axle axis and the main gear assembly is adapted to rotate about an axis generally perpendicular to the axle axis.

5. The system of claim 1 wherein the fastener comprises external threads adapted to engage internal threads of the through aperture.

6. A vertebral implant system comprising:
    a vertebral implant including
        an inner cylindrical assembly with a first bone engagement surface and
        a first outer cylindrical assembly with an outer wall and a second bone engagement surface sized to receive at least a portion of the inner cylindrical assembly such that the inner and outer cylindrical assemblies are coaxially aligned along an implant axis;
    an expansion device including
        an axle having proximal and distal end portions with an axle axis defined between the proximal and distal end portions;
        a gear rotatable about the axle axis at the proximal end portion of the axle; and
        a first fastener sized to extend into only one through aperture in the outer wall of the first outer cylindrical assembly;
    wherein the first fastener prevents the first outer cylindrical assembly from rotating relative to the expansion device when the vertebral implant expands along the implant axis in response to rotation of the gear.

7. The vertebral implant system of claim 6 wherein the vertebral implant further comprises a second outer cylindrical assembly sized to receive at least a portion of the inner cylindrical assembly.

8. The vertebral implant system of claim 6 wherein the expansion device further comprises a second fastener sized to extend into only one through aperture in an outer wall of the second outer cylindrical assembly, wherein the second fastener prevents the second outer cylindrical assembly from rotating relative to the expansion device when the vertebral implant expands along the implant axis in response to rotation of the gear.

9. The vertebral implant system of claim 8 further comprising:
    an outer casing through which the axle extends, and
    wherein the first and second fasteners are part of a holding instrument attached to the first and second outer cylindrical assemblies of the vertebral implant and further attached to the outer casing.

10. The vertebral implant system of claim 9 wherein the holding instrument further comprises:
a pair of parallel alignment arms for the attachment to the first and second outer cylindrical assemblies;
an attachment device for the attachment to the outer casing;
one or more expansion members extending between the attachment device and each alignment arm; and
an alignment member extending between the alignment arms for maintaining the parallel alignment of the alignment arms as the vertebral implant expands along the implant axis in response to rotation of the gear.

11. The vertebral implant system of claim 6 wherein the expansion device includes an engaging portion which includes a set of teeth for engaging the gear externally of the outer wall of the outer cylindrical assembly.

12. The vertebral implant system of claim 11 wherein the set of teeth are radially arranged about an axis generally perpendicular to the axle axis.

13. The vertebral implant system of claim 6 wherein the expansion device includes an engaging portion which includes a set of rotatable teeth for engaging the inner cylindrical assembly.

14. The vertebral implant system of claim 13 wherein the set of rotatable teeth are adapted to engage annularly spaced sockets in the inner cylindrical assembly.

15. The vertebral implant system of claim 6 wherein the fastener comprises external threads adapted to engage internal threads of the circular aperture.

16. A system comprising:
a vertebral implant comprising:
a tubular portion including a plurality of side wall openings; and
a pair of endplates such that the tubular body portion is bounded by the pair of endplates; and
an instrument comprising:
an axle defining a first axis and having a proximal end and a distal end, the axle adapted to rotate about the first axis;
a first gear connected to the axle and adapted to rotate about the first axis;
a second gear engaged with the first gear and adapted to rotate about a second axis generally perpendicular to the first axis;
a toothed section fixedly attached to and coaxially aligned with the second gear for conjoint rotation therewith about the second axis, the toothed section including a plurality of circumferentially spaced teeth,
wherein the circumferentially spaced teeth are configured to be received in at least of the plurality of side wall openings in the tubular body portion of the vertebral implant, and
wherein rotation of the axle is operative, via rotation of the circumferentially spaced teeth received in the tubular body portion side wall openings, to rotate the tubular body portion relative to the pair of endplates such that the tubular body portion and the pair of endplates remain within an intervertebral disc space when the vertebral implant is implanted.

17. The system of claim 16 further comprising:
an outer casing through which the axle extends, and
a holding instrument attached to the pair of endplates of the vertebral implant and further attached to the outer casing.

18. The system of claim 17 wherein the holding instrument further comprises:
a pair of parallel alignment arms for the attachment to the pair of endplates;
an attachment device for the attachment to the outer casing;
one or more expansion members extending between the attachment device and each alignment arm; and
an alignment member extending between the alignment arms for maintaining the parallel alignment of the alignment arms as the vertebral implant expands.

19. The instrument of claim 16 wherein rotation of the axle further causes the tubular body to move linearly relative to the pair of endplates along an axis defined by a vertebral column.

20. The instrument of claim 16 wherein rotation of the axle causes relative motion along a threaded connection between the tubular body and the pair of endplates.

* * * * *

UNITED STATES PATENT AND TRADEMARK OFFICE
CERTIFICATE OF CORRECTION

PATENT NO.        : 7,608,078 B2                                   Page 1 of 1
APPLICATION NO. : 11/286887
DATED             : October 27, 2009
INVENTOR(S)       : Bret M. Berry It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this

Twelfth Day of October, 2010

David J. Kappos
*Director of the United States Patent and Trademark Office*